Figure 1:
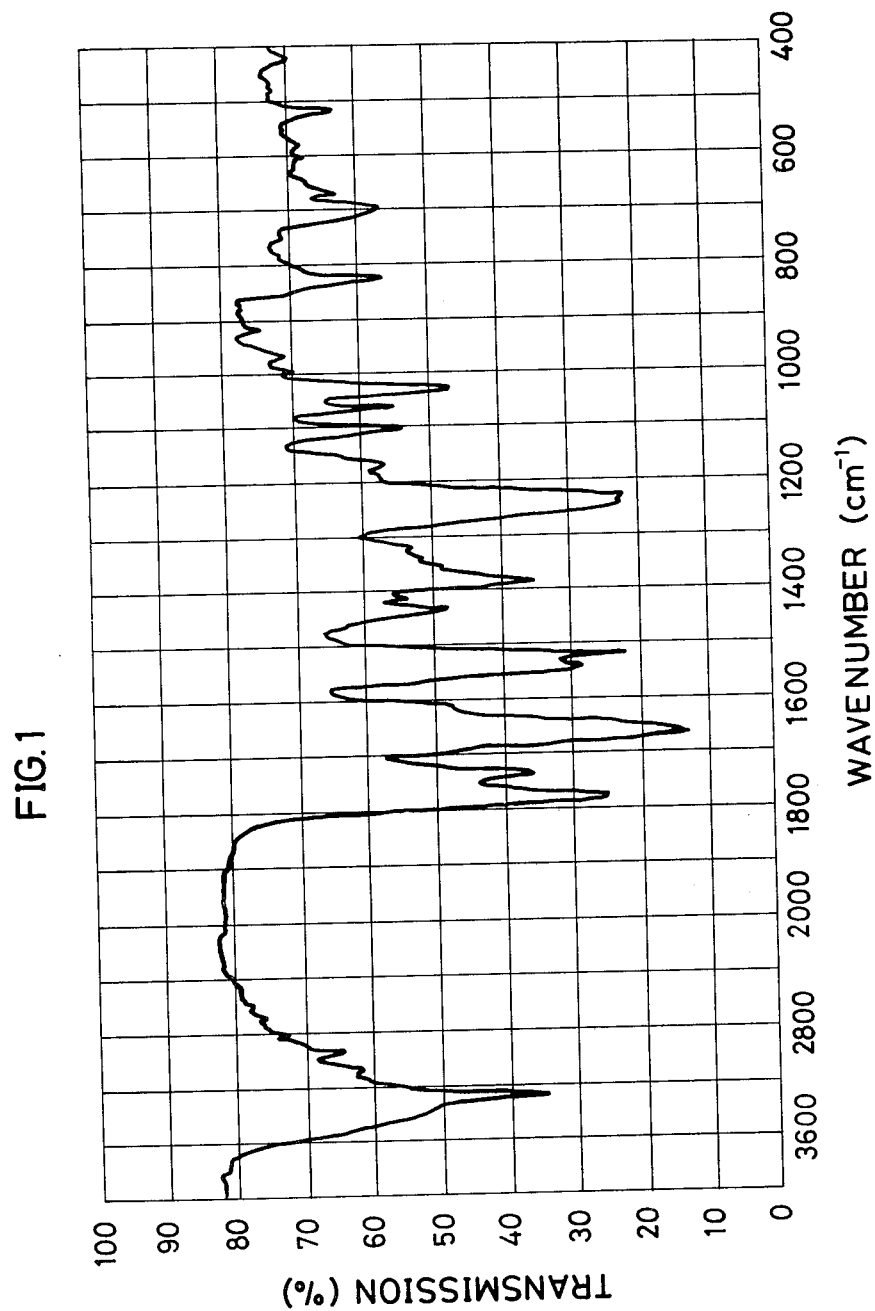

United States Patent [19]

Muto et al.

[11] 4,439,434
[45] Mar. 27, 1984

[54] CEPHALOSPORIN DERIVATIVE AND PHARMACEUTICAL COMPOSITION CONTAINING THE DERIVATIVE

[75] Inventors: Shigeaki Muto, Tokyo; Kouichi Niimura, Sayama; Takao Ando, Tokyo; Masahiko Fujii, Komae; Takao Furusho, Machida; Chikao Yoshikumi, Kunitachi, all of Japan

[73] Assignee: Kureha Kagaku Kogyo Kabushiki Kaisha, Nihonbashi, Japan

[21] Appl. No.: 418,761

[22] Filed: Sep. 16, 1982

[30] Foreign Application Priority Data

Sep. 18, 1981 [JP] Japan .................. 56-147577
Sep. 22, 1981 [JP] Japan .................. 56-149868

[51] Int. Cl.³ .................. A61K 31/545; C07D 501/34
[52] U.S. Cl. .................. 424/246; 544/28
[58] Field of Search .................. 544/28; 424/246

[56] References Cited

U.S. PATENT DOCUMENTS 3,635,953  1/1972  Wolf et al. .................. 544/28
3,641,015  2/1972  Lewis et al. .................. 544/28

Primary Examiner—Paul M. Coughlan, Jr.

[57] ABSTRACT

A compound having the general formula (I) is derived from a cephalosporin;

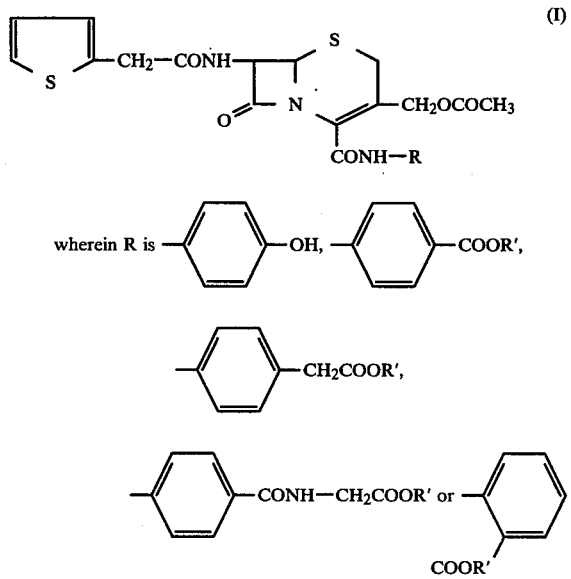

wherein R' is a hydrogen atom, an alkyl group having 1 to 4 carbon atoms or an alkali metal.

A pharmaceutical composition containing the compound is excellent in an antibacterial activity, the activity being recovered by the action of an activating enzyme in a living body although the compound per se shows a low activity against the beneficial bacterial colonies in a living body.

23 Claims, 10 Drawing Figures

CEPHALOSPORIN DERIVATIVE AND PHARMACEUTICAL COMPOSITION CONTAINING THE DERIVATIVE

The present invention relates to a compound derived from a cephalosporin and a pharmaceutical composition containing the compound as an active ingredient. In particular, the invention relates to a compound obtained by modifying chemically a cephalosporin which is one of antibiotics, an antibacterial activity of the compound being lost by such a chemical modification but recovered when the compound is absorbed into a living body, and to a pharmaceutical composition containing the compound as an active ingredient and exhibiting an activity similar to a cephalosporin in a living body.

An antibiotic which is so-called cephalosporin (hereinafter referred to as a cephalosporin antibiotic) are well known as an excellent drug due to its selective toxicity to bacteria. However, such a cephalosporin antibiotic has a serious defect, that is, it may disturb the beneficial bacterial colonies ordinarily present in living bodies, particularly the intestinal bacterial colonies, since it may also be antibacterially active against the beneficial bacteria. This defect is very serious when such a cephalosporin antibiotic is orally administered. As a result, "microbisme selectionné et substitué" is caused resulting in colitis and diarrhea.

It is an object of the invention to provide an antibiotic which does not have such a defect. An another object of the invention is to provide a compound derived from a cephalosporin antibiotic (hereinafter referred to as a cephalosporin derivative). A still another object of the invention is to provide a pharmaceutical exhibiting an activity similar to a cephalosporin antibiotic in a living body.

The cephalosporin derivative of the invention has the general formula (I);

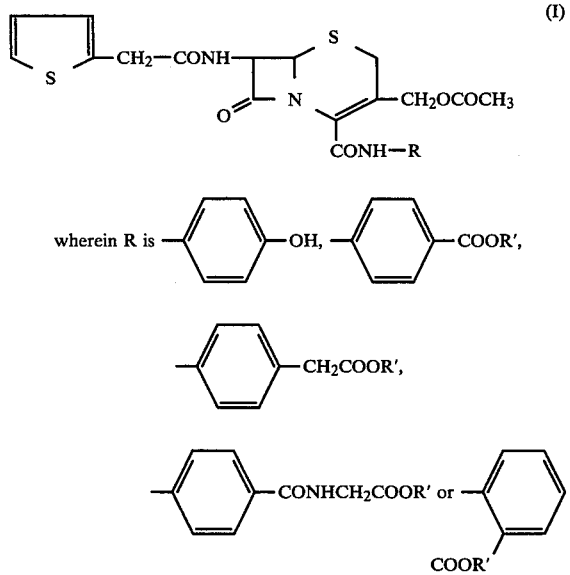

wherein R' is a hydrogen atom, an alkyl group having 1 to 4 carbon atoms or an alkali metal. The carbonyl group of the cephalosporin derivative may be in the form of a salt other than alkali metal salt, for example an alkali earth metal salt, an aluminum salt, an ammonium salt, and the like.

The cephalosporin derivative of the invention may be derived from a cephalosporin antibiotic by a chemical modification. The cephalosporin derivative is absorbed into a living body without affecting the bacterial colonies ordinarily present in living bodies and shows an antibacterial activity only when entering into blood in the living bodies, therefore, the cephalosporin derivative of the invention is an antibiotic of the new type quite different from the conventional cephalosporin antibiotics.

The cephalosporin derivative of the invention may be prepared by the following process.

7-(thienyl-2-acetamido)cephalosporanic acid having the formula (II);

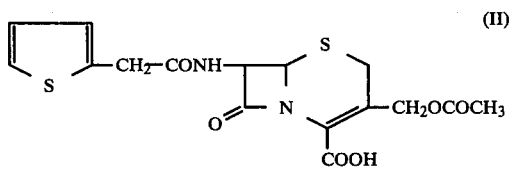

or a salt or a chloride thereof is dissolved in an organic solvent, for example, dimethylformamide (DMF), acetone, benzene, dichloromethane, pyridine, tetrahydrofuran (THF), dioxane, triethylamine, and the like. It is preferable to add as an activating agent to the system, for example, carbodiimide, ethyl chloroformate, oxalyl chloride, and the like. Into the obtained solution, an amine compound having the general formula (III);

wherein R is defined above is added and the reaction is carried out at the temperature of $-30°$ C. to $50°$ C. for 0.5 to 48 hours. The cephalosporin derivative of the invention is thereafter collected by the conventional method, for example, washing with a solvent, extraction with a solvent, recrystallization, and the like.

As seen from the Examples described hereinafter, the cephalosporin derivative of the invention has low toxicity and exhibits an antibacterial activity in a living body without affecting the intestinal bacterial colonies.

The cephalosporin derivative of the invention may be useful in the same field as the conventional cephalosporin antibiotics since the cephalosporin derivative is transformed into a cephalosporin antibiotic in a living body.

The cephalosporin derivative of the invention may be used singly as an antibacterial drug.

The cephalosporin derivative of the invention may be used as an active ingredient of a pharmaceutical composition. The pharmaceutical composition may contain a pharmaceutically acceptable carrier, diluent or adjuvant as well as at least one cephalosporin derivative of the invention and may be used in a dosage unit form. The composition may be administered orally or rectally or by injection. The dosage form for oral administration may be tablet, capsule, powder, granule, pill, ampoule, or the like.

The pharmaceutical composition may contain filler, extender, binder, wetting agent, disintegrant, retarder of dissolution, accelerator of absorption, adhesive carrier and/or lubricant, for example, starch, mannitol, silicic acid, cellulose derivative, gelatin, alginate, glycerol, agar, calcium carbonate, sodium hydrogen carbonate, paraffin, quartarnary ammonium compound, glycerol monostearate, kaolin, bentonite, talc, potassium stearate, magnesium stearate, polyethylene glycol, and the like.

The composition may be in the form of pharmaceutically acceptable emulsion, solution, suspension, or the like.

A suppository containing the cephalosporin derivative of the invention as an active ingredient may contain polyethylene glycol and/or fatty acid or ester thereof.

A syrup or elixir may contain an inert diluent such as water and paraffin and may be used as a liquid composition suitable for oral administration. These compositions may contain an adjuvant such as wetting agent, edulcorant and seasoning agent.

The composition for injection may be a sterilized aqueous or nonaqueous solution, suspension or emulsion and may contain, for example, propylene glycol, polyethylene glycol, olive oil, and the like.

The composition may contain 0.01 to 99.5% by weight, preferably 0.1 to 90% by weight of the cephalosporin derivative of the invention as an active ingredient.

The cephalosporin derivative of the invention may be useful for the same use as the conventional cephalosporin antibiotics and effective in treating an infectious disease due to bactria. The dose may depend on the degree of the infection and the state of the patient, and generally the dose of 0.1 to 10 g may be administered to an adult patient per one day, divided into several times.

The invention is illustrated in more detail in the following Examples which are not considered as limiting. It is apparent that many modifications and variations of the invention may be made without departing from the spirit and scope thereof.

EXAMPLE 1

Preparation of N-(4-hydroxyphenyl)-7-(thienyl-2-acetamido)cephalosporanic acid amide

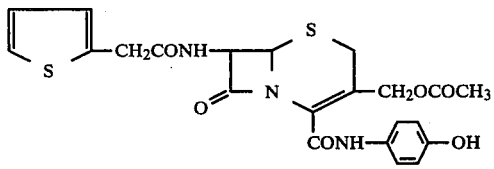

Into 50 ml of tetrahydrofuran (THF), 2.0 g of 7-(thienyl-2-acetamido)cephalosporanic acid, 0.55 g of 4-aminophenol and 1.05 g of N,N'-dicyclohexylcarbodiimide were dissolved and stirred at room temperature for 24 hours. The produced crystal in the reaction mixture was filtered out and washed several times with 30 ml of hot ethanol. The residue was recrystallized from ethanol and 1.4 g of powdery crystal was obtained with the yield of 70%.

Melting point (m.p.); 235°–238° C.

Infrared absorption bands (I.R.), $\nu_{max}$, in the unit of cm$^{-1}$ (KBr); 3280, 1784, 1735, 1663, 1518 and 1230, refer to also FIG. 1.

Ultraviolet absorption bands (U.V.) $\lambda_{max}$, in the unit of nm (CH$_3$CN); 232 and 274.

| Elementary analysis; | C (%) | H (%) | N (%) |
|---|---|---|---|
| Calculated as $C_{22}H_{21}O_6N_3S_2$; | 54.21 | 4.31 | 8.62 |
| Found; | 54.1 | 4.2 | 8.7. |

EXAMPLE 2

Preparation of N-(4-carbomethoxyphenyl)-7-(thienyl-2-acetamido)-cephalosporanic acid amide

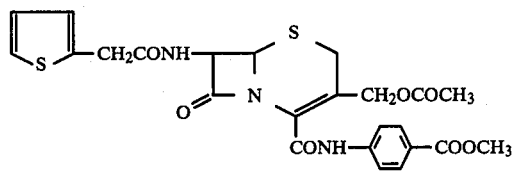

Into 10 ml of acetone was suspended 837 mg of sodium 7-(thienyl-2-acetamido)cephalosporanate. After adding 3 drops of pyridine to the suspension, 217 mg of ethyl chloroformate was added and stirred at 0° C. for 30 minutes. 302 mg of methyl p-aminobenzoate was further added to the suspension and the mixture was stirred overnight. After the reaction was over, the solvent was distilled off by evaporation. The residue was fully extracted by adding 30 ml of 1% solution of NaHCO$_3$ and 30 ml of ethyl acetate (3 times with 30 ml). The extract solution was washed with 30 ml of 0.01 N aqueous solution of HCl and further with 30 ml of water. The obtained solution in ethyl acetate was dried on Na$_2$SO$_4$, filtered on a filter paper and dried under reduced pressure. The obtained crude product was recrystallized from ethyl acetate/n-hexane and 244 mg of crystal was obtained with the yield of 23%.

M.p.; 198°–200° C.

Figure 2:
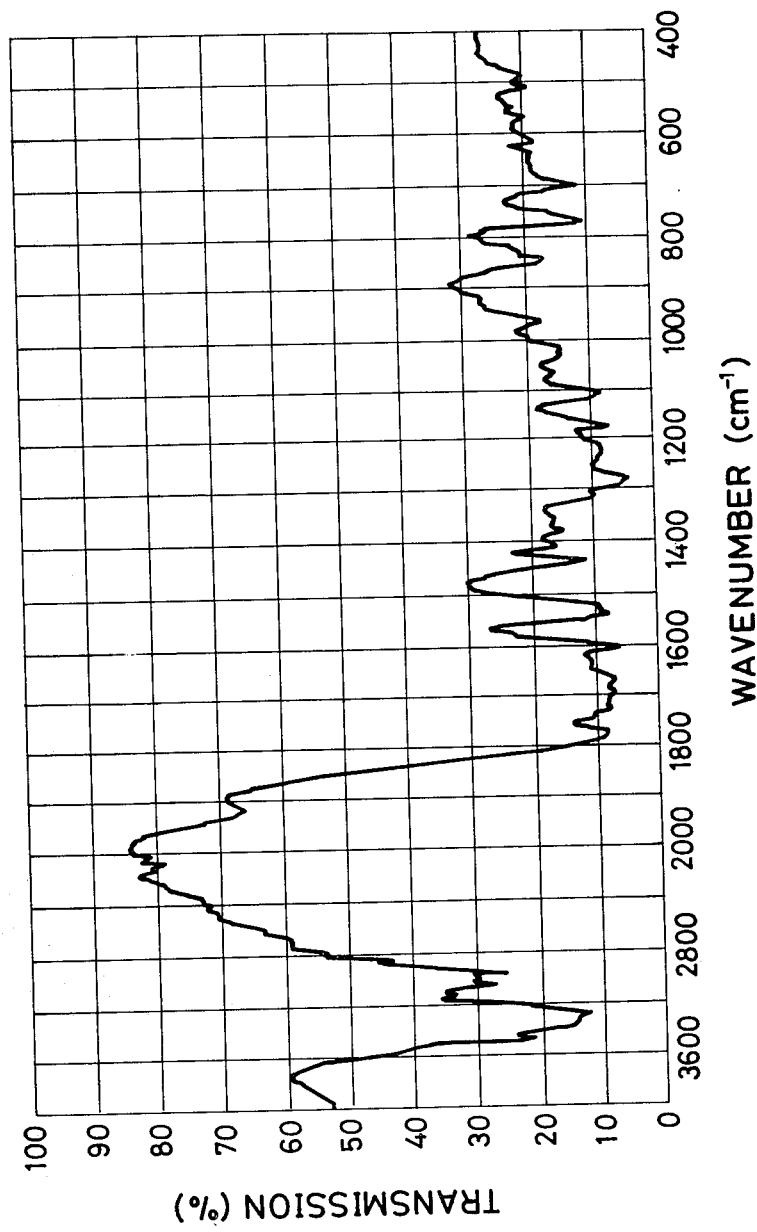

I.R. $\nu_{max}$, cm$^{-1}$ (KBr); 3290, 1790, 1729, 1603, 1539 and 1280, refer to also FIG. 2.

U.V. $\lambda_{max}$, nm (CH$_3$CN); 246 and 273.

| Elementary analysis; | C (%) | H (%) | N (%) |
|---|---|---|---|
| Calculated as $C_{24}H_{23}O_7N_3S_2$; | 54.42 | 4.38 | 7.94 |
| Found; | 54.5 | 4.4 | 8.2. |

EXAMPLE 3

Preparation of N-(4-carboethoxyphenyl)-7-(thienyl-2-acetamido)cephalosporanic acid amide

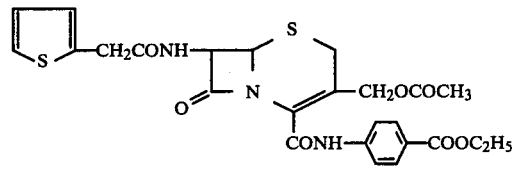

Into 100 ml of THF, 2.0 g of 7-(thienyl-2-acetamido)-cephalosporanic acid, 0.83 g of ethyl 4-aminobenzoate and 1.05 g of N,N'-dicyclohexylcarbodiimide were dissolved and stirred at room temperature for 24 hours. The produced N,N'-dicyclohexylurea was removed by filtration and the solvent was distilled off from the filtrate. The residue was dissolved into 100 ml of chloroform, washed with 5% aqueous solution of hydrochloric acid and then with water and dried on anhydrous magnesium sulfate. After distilling off solvent, the residue was recrystallized from a mixed solvent of ethyl acetate and n-hexane to obtain 1.1 g of crystal with the yield of 41%.

M.p.; 209°–211° C.

Figure 3:
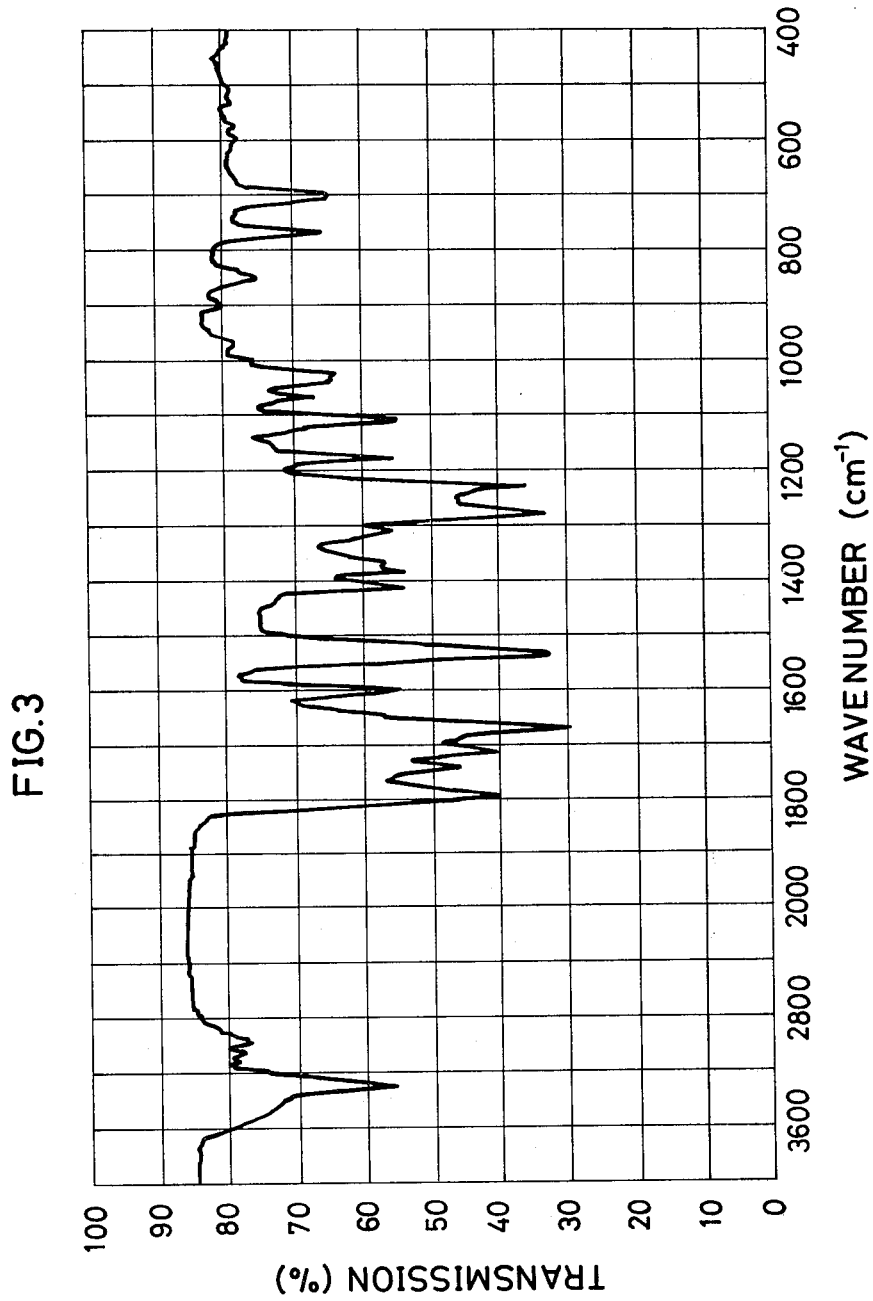

I.R. $\nu_{max}$, cm$^{-1}$(KBr); 3295, 1792, 1740, 1670, 1534 and 1277, see also FIG. 3.

U.V. $\lambda_{max}$, nm (CH$_3$CN); 236 and 273.

| Elementary analysis; | C (%) | H (%) | N (%) |
|---|---|---|---|
| Calculated as C$_{25}$H$_{25}$O$_7$N$_3$S$_2$; | 55.25 | 4.60 | 7.73 |
| Found; | 55.3 | 4.5 | 7.7. |

EXAMPLE 4

Preparation of
N-(4-carbo-n-butoxyphenyl)-7-(thienyl-2-acetamido)-cephalosporanic acid amide

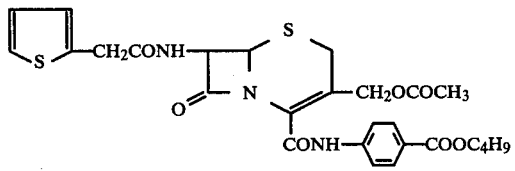

Into 100 ml of THF, 2.0 g of 7-(thienyl-2-acetamido)-cephalosporanic acid, 0.97 g of n-butyl 4-aminobenzoate and 1.05 g of N,N'-dicyclohexylcarbodiimide were dissolved and stirred at room temperature for 24 hours. After removing the formed N,N'-dicyclohexylurea by filtration, the solvent was distilled off from the filtrate and the residue was dissolved into 100 ml of chloroform. The solution in chloroform was washed with 5% aqueous solution of hydrochloric acid and then with water and thereafter dried on anhydrous magnesium sulfate. After the solvent was distilled off, the residue was recrystallized from a mixed solvent of ethyl acetate and n-hexane to obtain 1.2 g of crystal with the yield of 42%.

M.p.; 176°–177° C.

Figure 4:
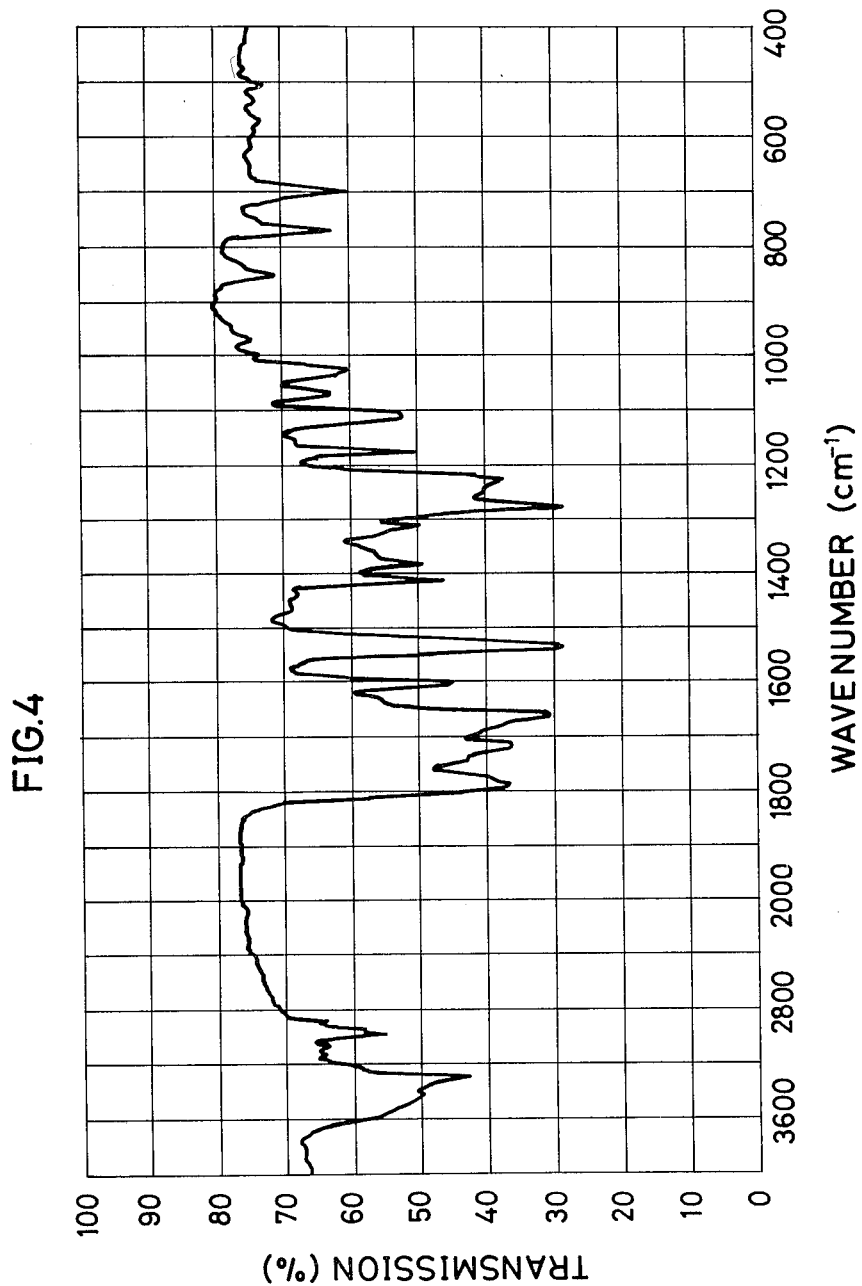

I.R. $\nu_{max}$, cm$^{-1}$ (KBr); 3290, 1785, 1717, 1663, 1535 and 1278, refer to also FIG. 4.

U.V. $\lambda_{max}$, nm (CH$_3$CN); 237 and 274.

| Elementary analysis; | C (%) | H (%) | N (%) |
|---|---|---|---|
| Calculated as C$_{27}$H$_{29}$O$_7$N$_3$S$_2$; | 56.74 | 5.08 | 7.36 |
| Found; | 56.8 | 5.1 | 7.2. |

EXAMPLE 5

Preparation of
N-(4-carboxymethylphenyl)-7-(thienyl-2-acetamido)-cephalosporanic acid amide

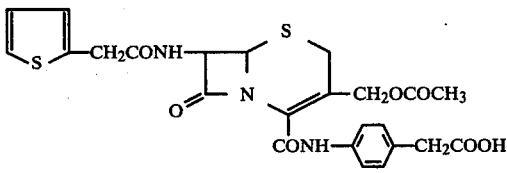

Into 100 ml of THF, 2.0 g of 7-(thienyl-2-acetamido)-cephalosporanic acid, 0.76 g of 4-aminophenylacetic acid and 1.05 g of N,N'-dicyclohexylcarbodiimide were dissolved and stirred at room temperature for 24 hours. After the formed N,N'-dicyclohexylurea was removed by filtration, the solvent was distilled off from the filtrate and the residue was dissolved into 100 ml of chloroform. The obtained solution in chloroform was washed with 5% aqueous solution of hydrochloric acid and then with water and dried on anhydrous magnesium sulfate. After distilling off the solvent, the residue was recrystallized from a mixed solvent of ethyl acetate and n-hexane to obtain 0.84 g of crystal with the yield of 32%.

M.p.; 140°–145° C. (decompose).

Figure 5:
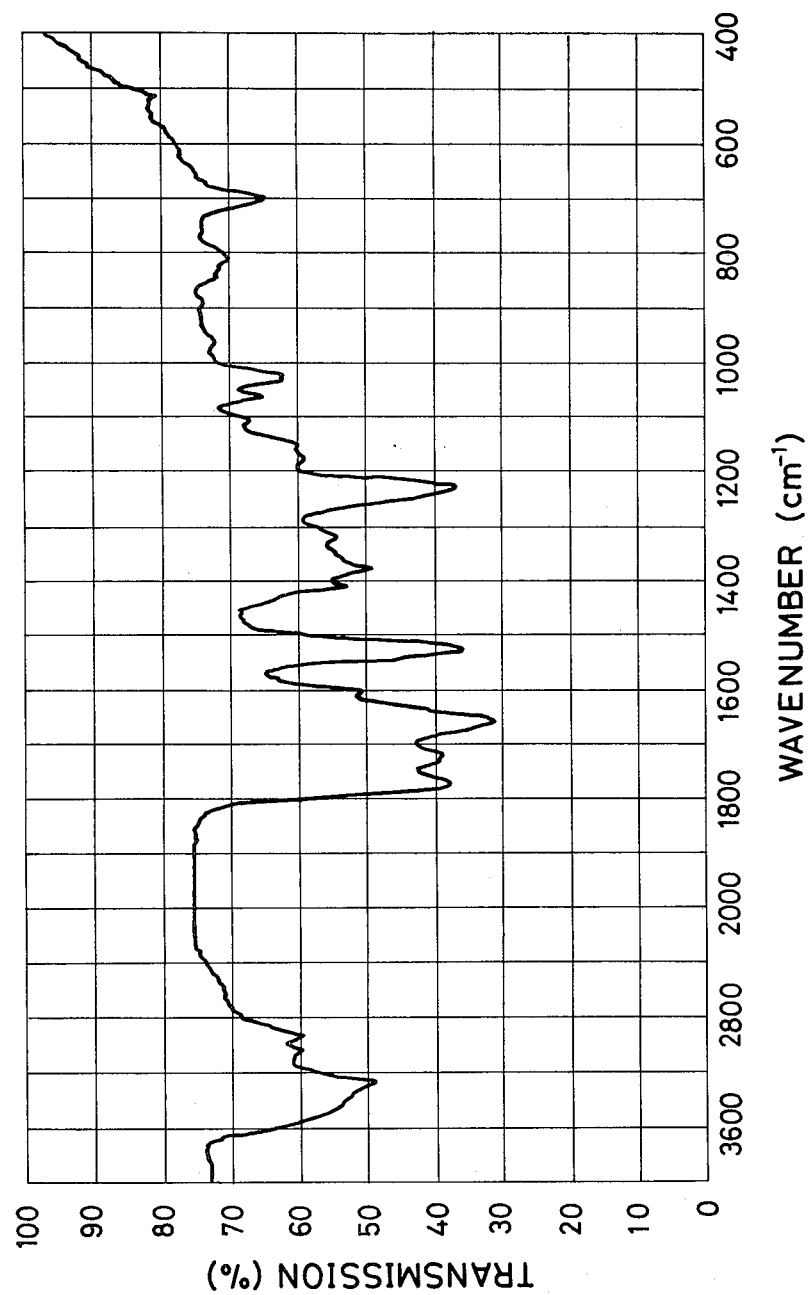

I.R. $\nu_{max}$, cm$^{-1}$ (KBr); 3270, 1773, 1720, 1660, 1529 and 1227, see also FIG. 5.

U.V. $\lambda_{max}$, nm (CH$_3$CN); 237 and 272.

| Elementary analysis; | C (%) | H (%) | N (%) |
|---|---|---|---|
| Calculated as C$_{24}$H$_{23}$O$_7$N$_3$S$_2$; | 54.44 | 4.35 | 7.94 |
| Found; | 54.4 | 4.4 | 7.9. |

EXAMPLE 6

Preparation of
N-(4-carbomethoxymethylphenyl)-7-(thienyl-2-acetamido)cephalosporanic acid amide

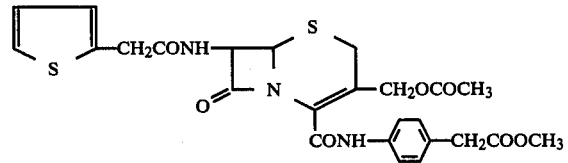

Into 50 ml of THF, 2.0 g of 7-(thienyl-2-acetamido)-cephalosporanic acid, 0.83 g of methyl 4-aminophenylacetate and 1.05 g of N,N'-dicyclohexylcarbodiimide were dissolved and stirred at room temperature for 24 hours. The produced crystal in the reaction mixture was filtered out and washed with 30 ml of hot ethanol several times. The residue was recrystallized from ethanol to obtain 1.5 g of powdery crystal with the yield of 56%.

M.p.; 216°–217° C.

Figure 6:
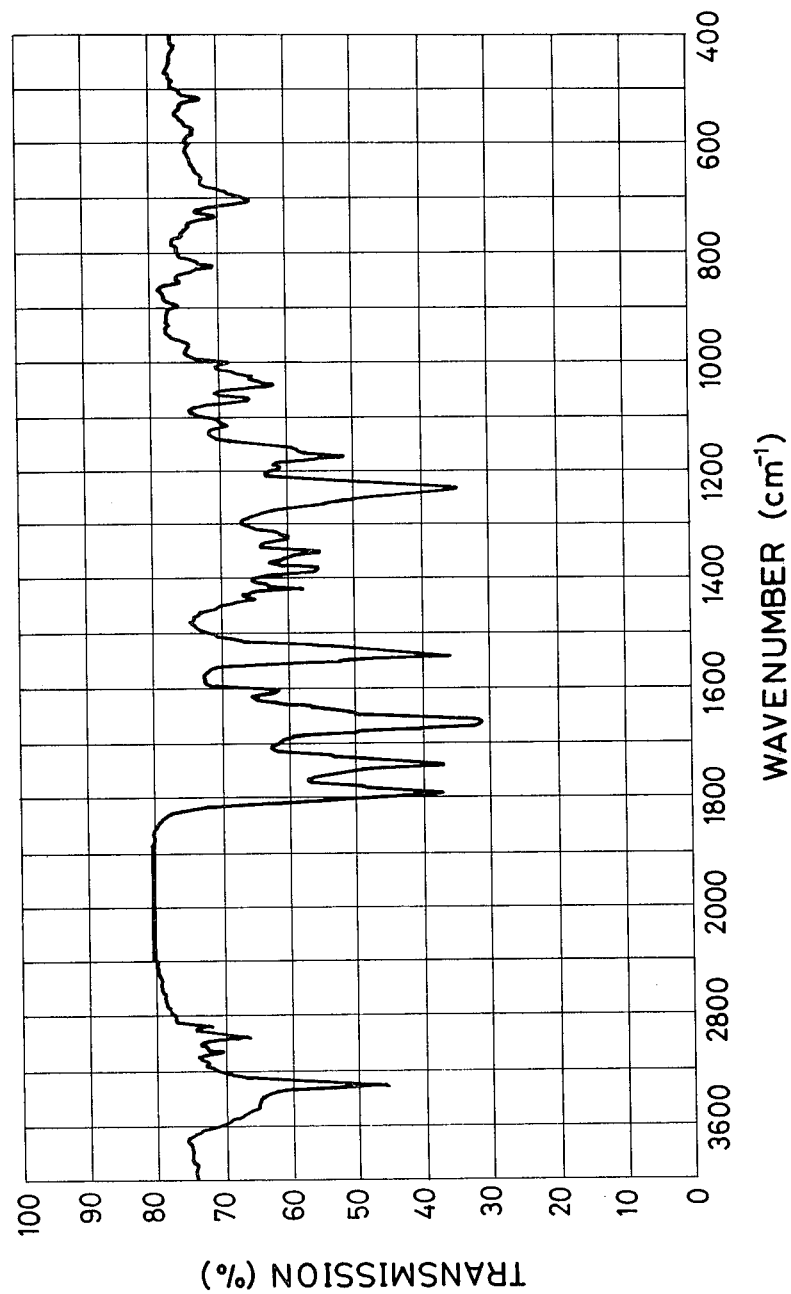

I.R. $\nu_{max}$, cm$^{-1}$ (KBr); 3300, 1790, 1740, 1660, 1540 and 1231, refer to also FIG. 6.

U.V. $\lambda_{max}$, nm (CH$_3$CN); 237 and 273.

| Elementary analysis; | C (%) | H (%) | N (%) |
|---|---|---|---|
| Calculated as $C_{25}H_{25}O_7N_3S_2$; | 55.25 | 4.60 | 7.73 |
| Found; | 55.3 | 4.5 | 7.8 |

EXAMPLE 7

Preparation of N-(4-carboethoxymethylphenyl)-7-(thienyl-2-acetamido)cephalosporanic acid amide

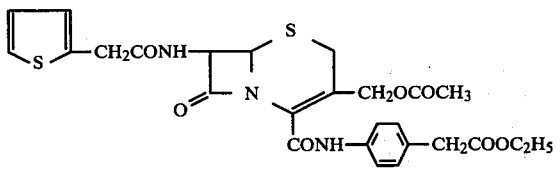

Into 50 ml of THF, 2.0 g of 7-(thienyl-2-acetamido)-cephalosporanic acid, 0.9 g of ethyl 4-aminophenylacetate and 1.05 g of N,N'-dicyclohexylcarbodiimide were dissolved and stirred at room temperature for 24 hours. The formed crystal in the reaction mixture was filtered out and washed with 30 ml of hot ethanol several times. The residue was recrystallized from ethanol to obtain 1.7 g of powdery crystal with the yield of 61%.

M.p.; 207°–208° C.

Figure 7:
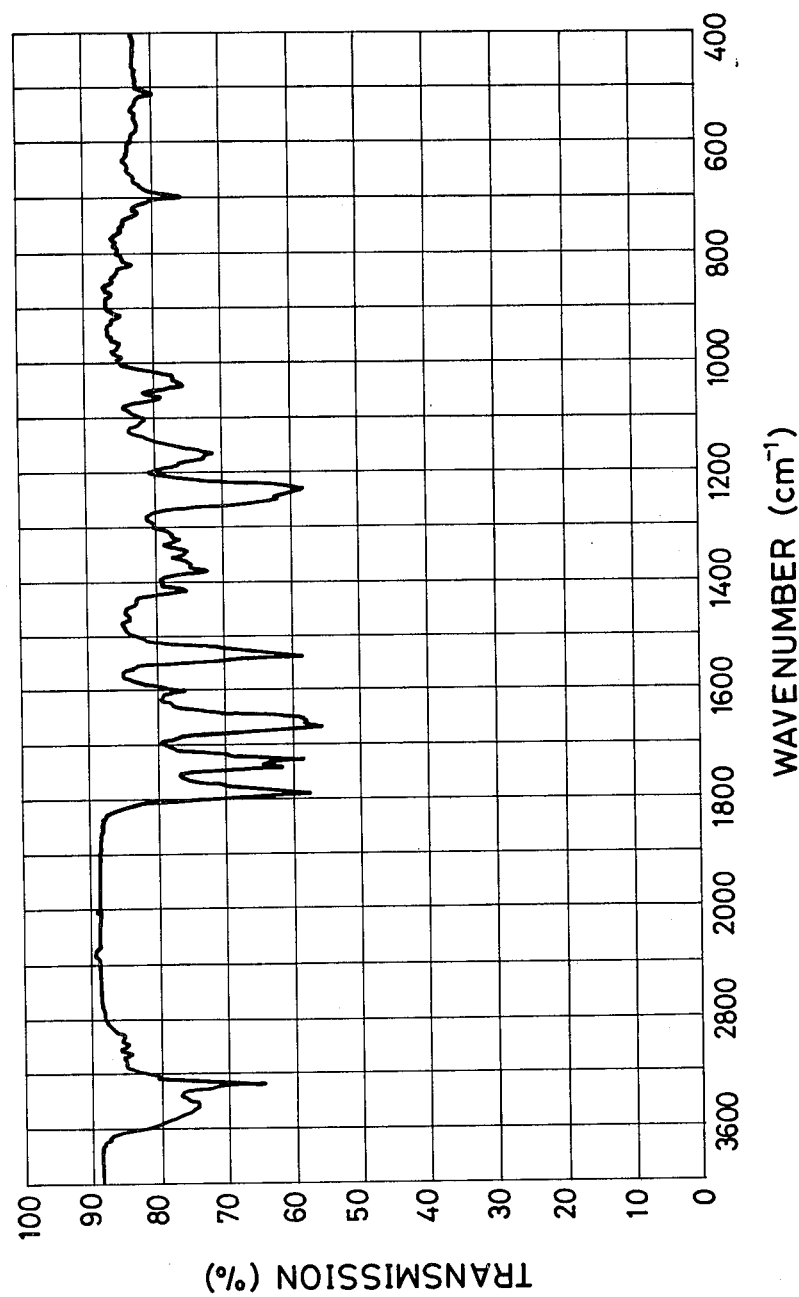

I.R. $\nu_{max}$, cm$^{-1}$ (KBr); 3280, 1785, 1725, 1660, 1537 and 1233, see also FIG. 7.

U.V. $\lambda_{max}$, nm (CH$_3$CN); 237 and 272.

| Elementary analysis; | C (%) | H (%) | N (%) |
|---|---|---|---|
| Calculated as $C_{26}H_{27}O_7N_3S_2$; | 56.01 | 4.85 | 7.54 |
| Found; | 56.1 | 4.9 | 7.5 |

EXAMPLE 8

Preparation of N-(4-carboxymethylcarbamoylphenyl)-7-(thienyl-2-acetamido)cephalosporanic acid amide

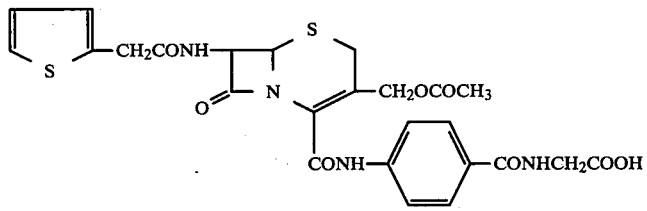

Into 100 ml of THF, 2.0 g of 7-(thienyl-2-acetamido)-cephalosporanic acid, 0.97 g of 4-aminohippuric acid and 1.05 g of N,N'-dicyclohexylcarbodiimide were dissolved and stirred at room temperature for 24 hours. After the formed N,N'-dicyclohexylurea was filtered out, the solvent was distilled off from the filtrate and the residue was dissolved in 100 ml of chloroform. The obtained solution in chloroform was washed with 5% aqueous solution of hydrochloric acid and then with water and dried on anhydrous magnesium sulfate. After the solvent was distilled off, the residue was recrystallized from a mixed solvent of ethyl acetate and n-hexane to obtain 0.94 g of crystal with the yield of 33%.

M.p.; 194°–196° C.

Figure 8:
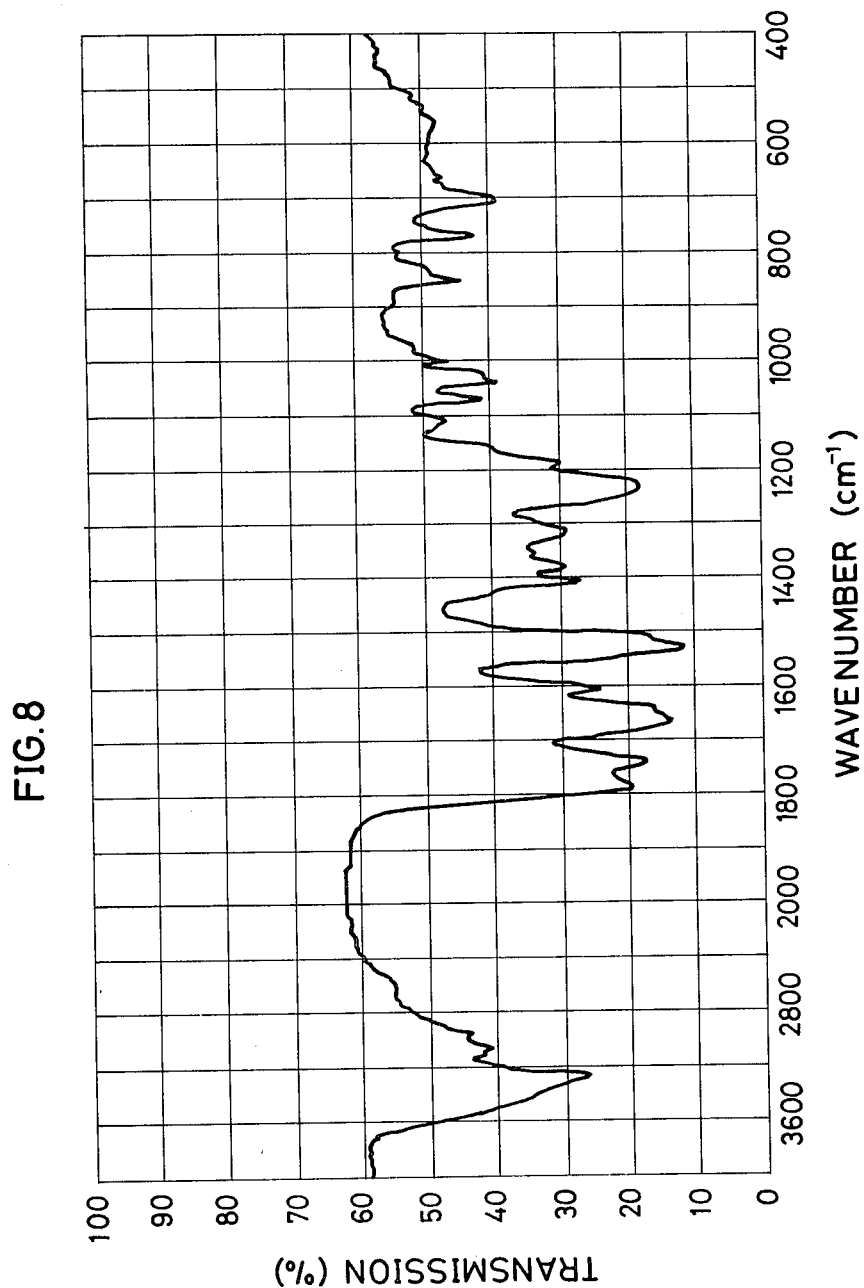

I.R. $\nu_{max}$, cm$^{-1}$ (KBr); 3280, 1785, 1739, 1665, 1532 and 1230, refer to also FIG. 8.

U.V. $\lambda_{max}$, nm (CH$_3$CN); 237 and 273.

| Elementary analysis; | C (%) | H (%) | N (%) |
|---|---|---|---|
| Calculated as $C_{25}H_{24}O_8N_4S_2$; | 53.45 | 4.20 | 9.79 |
| Found; | 52.4 | 4.1 | 9.8 |

EXAMPLE 9

Preparation of N-(4-carbomethoxymethylcarbamoylphenyl)-7-(thienyl-2-acetamido)cephalosporanic acid amide

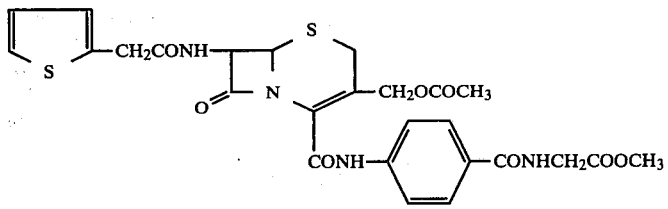

Into 50 ml of THF, 2.0 g of 7-(thienyl-2-acetamido)-cephalosporanic acid, 1.1 g of methyl 4-aminohippurate and 1.05 g of N,N'-dicyclohexylcarbodiimide were dissolved and stirred at room temperature for 24 hours. The produced crystal in the reaction mixture was filtered out and washed with 30 ml of hot ethanol several times. The residue was recrystallized from ethanol to obtain 1.6 g of powdery crystal with the yield of 54%.

M.p.; 229°–231° C.

Figure 9:
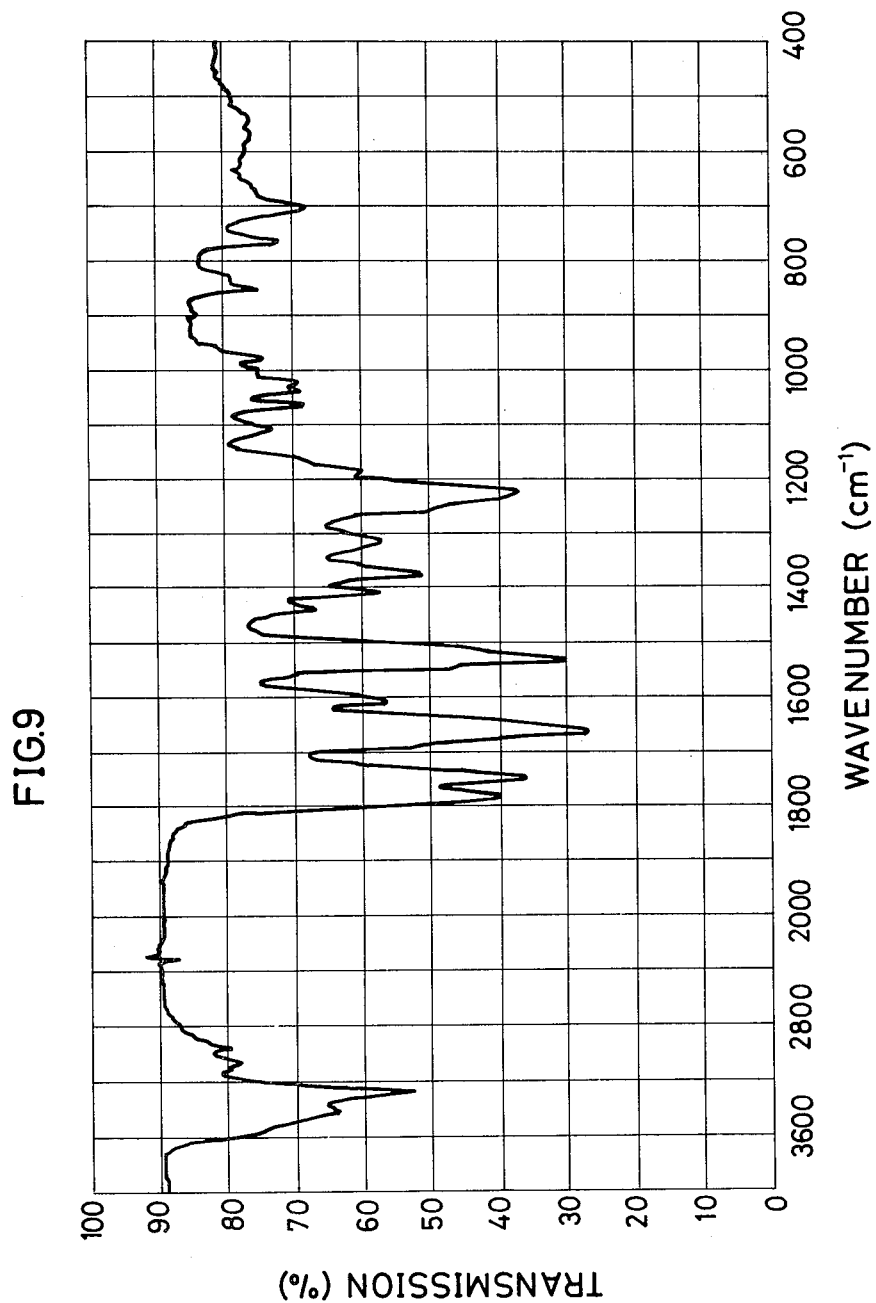

I.R. $\nu_{max}$, cm$^{-1}$ (KBr); 3280, 1781, 1748, 1664, 1533 and 1225, see also FIG. 9.

U.V. $\lambda_{max}$, nm (CH$_3$CN); 237 and 273.

| Elementary analysis; | C (%) | H (%) | N (%) |
|---|---|---|---|
| Calculated as $C_{26}H_{26}O_8N_4S_2$; | 53.24 | 4.44 | 9.56 |
| Found; | 53.3 | 4.4 | 9.6 |

EXAMPLE 10

Preparation of N-(2-carbomethoxyphenyl)-7-(thienyl-2-acetamido)-cephalosporanic acid amide

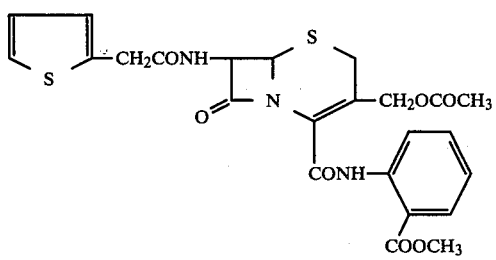

Into 100 ml of THF, 2.0 g of 7-(thienyl-2-acetamido)-cephalosporanic acid, 0.71 g of methyl 2-aminobenzoate and 1.05 g of N,N'-dicyclohexylcarbodiimide were dissolved and stirred at room temperature for 24 hours. After removing the formed N,N'-dicyclohexylurea by filtration, the solvent was distilled off from the filtrate and the residue was dissolved into 100 ml of chloroform. The obtained solution in chloroform was washed with 5% aqueous solution of hydrochloric acid and then with water and dried on anhydrous magnesium sulfate. After distilling off the solvent, the residue was recrystallized from a mixed solvent of ethyl acetate and n-hexane to obtain 0.92 g of crystal with the yield of 35%.

M.p.; 219°-220° C.

Figure 10:
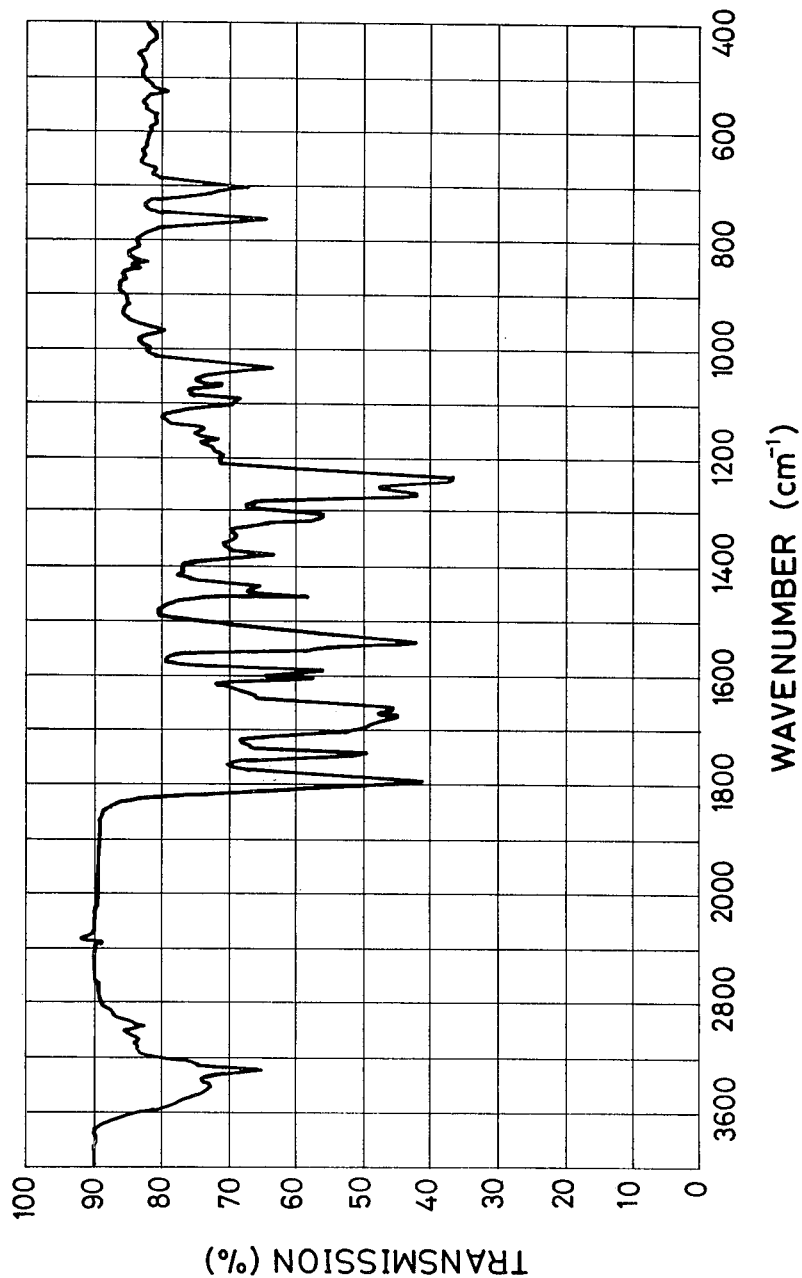

I.R. $\nu_{max}$, cm$^{-1}$ (KBr); 3280, 1792, 1740, 1675, 1658, 1537 and 1235, refer to also FIG. 10.

U.V. $\lambda_{max}$, nm (CH$_3$CN); 232, 273 and 311.

| Elementary analysis; | C (%) | H (%) | N (%) |
|---|---|---|---|
| Calculated as C$_{24}$H$_{23}$O$_7$N$_3$S$_2$; | 54.44 | 4.35 | 7.94 |
| Found; | 54.1 | 4.2 | 8.0 |

EXAMPLE 11

Acute toxicity

Each of the cephalosporin derivatives of the invention prepared in Examples 1 to 10 was dispersed in a physiological saline solution. The dispersion was administered to an ICR-JCL mouse orally by a stomach sonde or intraperitoneally by injection at a predetermined amount.

After administration, the intoxication symptom was continuously observed for a week and both intravital and died mice were dissected and observed. LD$_{50}$ value was obtained from the cumulative mortality of the treated mice by applying the data to the Litchfield-Wilcoxon's graphycal method. All cephalosporin derivatives of the invention gave LD$_{50}$ value of more than 10 g/kg in both oral and intraperitoneal administrations. The LD$_{50}$ value of cephalotin sodium (a conventional cephalosporin antibiotic) is about 5 g/kg.

EXAMPLE 12

Effect on the intestinal bacterial colonies

Each of the cephalosporin derivatives of the invention prepared in Examples 1 to 10 was orally administered to mice (one group consisting of five female ICR mice of 6-week-old) for two consecutive days at a dose of 500 mg/kg/day.

Before and one day after the administration, feces of each mouse were collected and diluted with an anaerobic diluent (phosphoric buffer solution) of 100 times volume and the diluted feces were ground. 0.1 ml of the diluted and ground feces was smeared on each culture medium shown in Table 1 and cultured aerobically or anaerobically (according to the anaerobic glove box method) under each condition shown in Table 1 and the number of each bacterium shown in Table 1 was counted.

The results are shown in Table 2.

As seen from Table 2, the number of Escherichia coli showed no remarkable change as compared to that before administration in the case of the cephalosporin derivative of the invention, while that number increased in the case of the comparative antibiotic, cephalotin. Furthermore, Lactobacillus acidophilus decreased in the case of cephalotin while such a decrease was not observed in the case of the cephalosporin derivative of the invention.

These results show that the cephalosporin derivative of the invention does not affect the intestinal bacterial colonies.

TABLE 1

Culture medium and culture condition of bacteria

| Bacterium | Culture medium | Culture condition |
|---|---|---|
| Escherichia coli | DHL agar | aerobic, 37° C., one day |
| Pseudomonas aeruginosa | NAC agar | aerobic, 37° C., one day |
| Streptococcus spp. | TATAC agar | aerobic, 37° C., one day |
| Lactobacillus acidophilus | LBS agar | anaerobic, 37° C., five days |
| Lactobacillus bifidus | BS agar | anaerobic, 37° C., five days |
| Bacteroides | NBGT agar | anaerobic, 37° C., five days |

TABLE 2

Logarithmic value of the number of bacterial cells per one g of feces

| Example No. | E. coli | Ps. aeruginosa | Strept. spp. | L. acidophilus | L. bifidus | Bacteroides |
|---|---|---|---|---|---|---|
| 1 | 6.5 | <3.0 | 6.3 | 8.9 | 8.2 | 8.7 |
| 2 | 6.4 | <3.0 | 6.7 | 9.1 | 8.6 | 8.1 |
| 3 | 6.5 | <3.0 | 6.5 | 9.0 | 8.3 | 8.1 |
| 4 | 6.4 | <3.0 | 6.7 | 9.1 | 8.5 | 8.1 |
| 5 | 6.5 | <3.0 | 6.8 | 9.1 | 8.4 | 8.2 |
| 6 | 6.8 | <3.0 | 6.5 | 8.9 | 8.3 | 8.8 |
| 7 | 6.4 | <3.0 | 6.6 | 8.9 | 8.3 | 8.8 |
| 8 | 6.4 | <3.0 | 6.8 | 9.1 | 8.5 | 8.1 |
| 9 | 6.5 | <3.0 | 7.1 | 9.3 | 8.6 | 8.1 |
| 10 | 6.5 | <3.0 | 6.4 | 9.0 | 8.2 | 8.0 |
| Before administration | 6.4 | <3.0 | 6.8 | 9.0 | 8.4 | 8.3 |
| Cephalotin | 9.9 | <3.0 | 9.0 | 4.1 | 9.2 | 7.2 |

EXAMPLE 13

Antibacterial activity

Antibacterial activity of each of the cephalosporin derivatives of the invention prepared in Examples 1 to 10 was examined against the following two bacteria according to the standard method of Japan Society of Chemitherapy: *Escherichia coli* IFO 12734 and *Staphylococcus aureus* IAM 1011.

Each bacterial strain was inoculated into the Mueller-Hinton's culture medium and cultured at 37° C. for 18 to 48 hours. The cultured medium was diluted so as to contain $1\times10^6$ cells of the bacteria per one ml, and the obtained medium was used as the bacterial specimen.

Agar plates were prepared by adding one part by weight of each solution of the cephalosporin derivative of the invention at a predetermined concentration to nine parts by weight of Mueller-Hinton's culture medium.

A loopful amount of the bacterial specimen prepared above was smeared to make a streak of about 2 cm on each agar plate prepared above and cultured at 37° C. for 18 to 24 hours.

The minimum concentration for completely inhibiting proliferation of the bacteria (referred to as MIC) was determined.

The results are shown in Table 3.

TABLE 3

| Example No. | MIC | |
|---|---|---|
| | E. coli | Staph. aureus |
| 1 | ≧100 | ≧12.5 |
| 2 | ≧25 | 0.2 |
| 3 | ≧100 | ≧12.5 |
| 4 | ≧100 | ≧12.5 |
| 5 | ≧100 | 1.56 |
| 6 | ≧100 | ≧12.5 |
| 7 | ≧100 | 6.25 |
| 8 | ≧100 | 12.5 |
| 9 | ≧100 | ≧12.5 |
| 10 | ≧100 | ≧12.5 |

EXAMPLE 14

The cephalosporin derivative of the invention was examined in the following experiment in order to prove that the cephalosporin derivative is activated in a living body.

As an activating enzyme of metabolism, a rat liver homogenate (S-9, manufactured by Oriental Yeast Company, Japan) was used in the following composition per 1 ml (hereinafter referred to as S-9 mix).
S-9: 0.5 ml
KCl: 3.3 μmol
MgCl$_2$.6H$_2$O: 8 μmol
Glucose 6-phosphate: 5 μmol
NADH: 4 μmol
NADPH: 4 μmol
0.2 M phosphoric buffer solution (pH of 7.4): 0.5 ml
0.1 ml of the solution of each of the cephalosporin derivatives of the invention prepared in Examples 1 to 10 at a concentration of 100 μg/ml was mixed with 0.9 ml of S-9 mix or 0.9 ml of 0.1 M phosphoric buffer solution (as a control) and the obtained mixture was incubated at 37° C. for 20 min. with shaking.

*Staphylococcus aureus* IAM 1011 was inoculated into a Mueller-Hinton's culture medium and cultured at 37° C. for 18 hours. The culture medium was adjusted to a cell concentration of $1\times10^8$ per 1 ml and mixed with 50 times by volume of Mueller-Hinton's agar culture medium to obtain an agar plate.

A penicillin cup of 8 mm in diameter was placed on the agar plate prepared above, and into the cup 0.1 ml of the mixture containing the cephalosporin derivative prepared above was introduced and allowed to stand at 4° C. for 2 hours, and then cultured at 37° C. for 18 hours to measure the diameter of a circle in which the proliferation of bacteria was inhibited (proliferation-inhibiting circle). The results are shown in Table 4. In Table 4, the proliferation-inhibiting index is shown in the ratio (%) of the diameter of the proliferation-inhibiting circle obtained by using each of the cephalosporin derivatives of the invention to that obtained by using each of the starting compound in preparing each of the cephalosporin derivatives of the invention.

| Index | % |
|---|---|
| − | 0 |
| ± | 0–1 |
| + | 1–33 |
| ++ | 33–66 |
| +++ | 66–100 |

TABLE 4

| | Proliferation-inhibiting index (%) | |
|---|---|---|
| Example No. | Before adding S-9 mix (control) | After adding S-9 mix |
| 1 | − | +++ |
| 2 | + | ++ |
| 3 | + | ++ |
| 4 | + | ++ |
| 5 | + | +++ |
| 6 | − | +++ |
| 7 | − | +++ |
| 8 | + | ++ |
| 9 | − | +++ |
| 10 | − | + |

As seen from Table 4, the cephalosporin derivative of the invention is activated by an enzyme in a living body to recover the antibacterial activity, although the cephalosporin derivative of the invention per se shows only low antibacterial activity in the absence of an activating enzyme.

EXAMPLE 15

*Escherichia coli* IFO 12734 ($1.4\times10^8$ cells) was inoculated intraperitoneally to ddY-SPF mice (a group consisting of 20 mice). Just after and 4 hours after the infection, each of the cephalosporin derivatives of the invention prepared in Examples 1 to 10 was administered orally at a dose of 500 mg/kg, and the mortality of the mice due to infection was observed for 7 days. More than 35% of the mice administered with the cephalosporin derivative of the invention survived even on the 7th day after the infection, although all mice without administration of the cephalosporin derivative of the invention died on 2nd day after infection.

The results show that the cephalosporin derivative of the invention is effective for oral administration against an infectious disease.

EXAMPLE 16

Formulation (1) Tablet

A tablet was prepared by a following composition in one tablet of 200 mg;
the cephalosporin derivative prepared in Example 6: 175 mg;
lactose: 16 mg;
starch: 5 mg;
hydroxypropylcellulose: 3 mg;
magnesium stearate: 1 mg.

The cephalosporin derivative of the invention and lactose was mixed and then an aqueous solution of hydroxypropylcellulose was admixed, and the mixture was kneaded, dried and pulverized. The magnesium stearate preliminarily dispersed into starch was admixed and the mixture was tabletted by the conventional method.

(2) Granule

A granule was prepared from a following composition;
the cephalosporin derivative prepared in Example 7: 176 mg;
lactose: 16 mg;
starch: 4 mg;
hydroxypropylcellulose: 4 mg.

The cephalosporin derivative of the invention, starch and lactose were mixed, and an aqueous solution of hydroxypropylcellulose was admixed, and the mixture was dried and pulverized. The pulverized mixture was sifted by 12 to 48 mesh sieves to obtain a granule.

What is claimed is:

1. A cephalosporin derivative having the general formula (I);

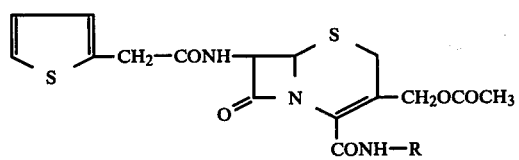

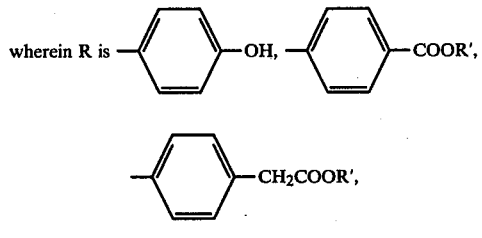

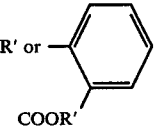

wherein R' is a hydrogen atom, an alkyl group having 1 to 4 carbon atoms or an alkali metal.

2. The derivative of claim 1, which is N-(4-hydroxyphenyl)-7-(thienyl-2-acetamido)cephalosporanic acid amide.

3. The derivative of claim 1, which is N-(4-carbomethoxyphenyl)-7-(thienyl-2-acetamide)cephalosporanic acid amide.

4. The derivative of claim 1, which is N-(4-carboethoxyphenyl)-7-(thienyl-2-acetamido)cephalosporanic acid amide.

5. The derivative of claim 1, which is N-(4-carbo-n-butoxyphenyl)-7-(thienyl-2-acetamido)cephalosporanic acid amide.

6. The derivative of claim 1, which is N-(4-carboxymethylphenyl)-7-(thienyl-2-acetamido)cephalosporanic acid amide.

7. The derivative of claim 1, which is N-(4-carbomethoxymethylphenyl)-7-(thienyl-2-acetamido)cephalosporanic acid amide.

8. The derivative of claim 1, which is N-(4-carboethoxymethylphenyl)-7-(thienyl-2-acetamido)cephalosporanic acid amide.

9. The derivative of claim 1, which is N-(4-carboxymethylcarbamoylphenyl)-7-(thienyl-2-acetamido)-cephalosporanic acid amide.

10. The derivative of claim 1, which is N-(4-carbomethoxymethylcarbamoylphenyl)-7-(thienyl-2-acetamido)cephalosporanic acid amide.

11. The derivative of claim 1, which is N-(2-carbomethoxyphenyl)-7-(thienyl-2-actamido)cephalosporanic acid amide.

12. A pharmaceutical composition in dosage unit form comprising 0.01 to 99.5% by weight of a cephalosporin derivative having the formula (I):

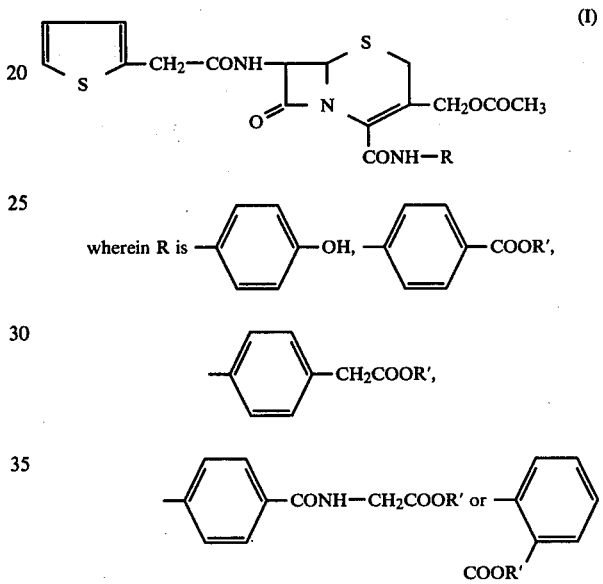

wherein R' is a hydrogen atom, an alkyl group having 1 to 4 carbon atoms or an alkali metal, and a pharmaceutically acceptable carrier therefor.

13. The pharmaceutical composition of claim 12, wherein the cephalosporin derivative is N-(4-hydroxyphenyl)-7-(theinyl-2-acetamido)cephalosporanic acid amide.

14. The pharmaceutical composition of claim 12, wherein the cephalosporin derivative is N-(4-carbomethoxyphenyl)-7-(thienyl-2-acetamido)-cephalosporanic acid amide.

15. The pharmaceutical composition of claim 12, wherein the cephalosporin derivative is N-(4-carboethoxyphenyl)-7-(thienyl-2-acetamido)-cephalosporanic acid amide.

16. The pharmaceutical composition of claim 12, wherein the cephalosporin derivative is N-(4-carbo-n-butoxyphenyl)-7-(thienyl-2-acetamido)cephalosporanic acid amide.

17. The pharmaceutical composition of claim 12, wherein the cephalosporin derivative is N-(4-carboxymethylphenyl)-7-(thienyl-2-acetamido)cephalosporanic acid amide.

18. The pharmaceutical composition of claim 12, wherein the cephalosporin derivative is N-(4-carbomethoxymethylphenyl)-7-(thienyl-2-acetamido)cephalosporanic acid amide.

19. The pharmaceutical composition of claim 12, wherein the cephalosporin derivative is N-(4-carboethoxymethylphenyl)-7-(thienyl-2-acetamido)cephalosporanic acid amide.

20. The pharmaceutical composition of claim 12, wherein the cephalosporin derivative is N-(4-carboxymethylcarbamoylphenyl)-7-(thienyl-2-acetamido)-cephalosporanic acid amide.

21. The pharmaceutical composition of claim 12, wherein the cephalosporin derivative is N-(4-carbomethoxymethylcarbamoylphenyl)-7-(thienyl-2-acetamido)cephalosporanic acid amide.

22. The pharmaceutical composition of claim 12, wherein the cephalosporin derivative is N-(2-carbomethoxyphenyl)-7-(thienyl-2-acetamido)cephalosporanic acid amide.

23. An antibacterial drug comprising 0.01 to 99.5% by weight of a cephalosporin derivative having the formula (I);

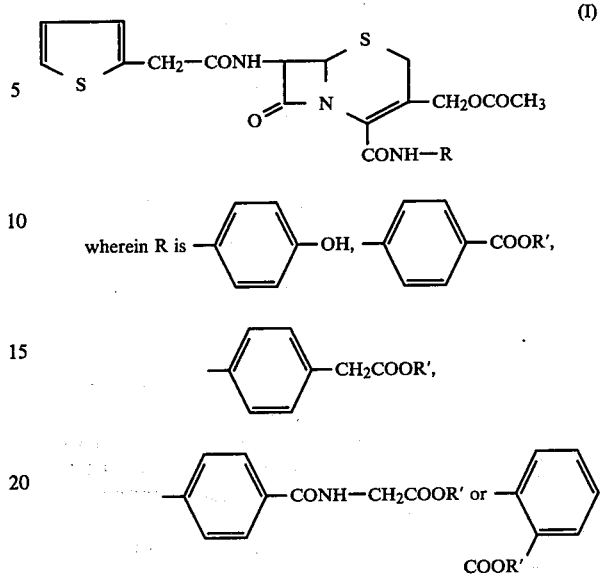

wherein R' is a hydrogen atom, an alkyl group having 1 to 4 carbon atoms or an alkali metal, and a pharmaceutically acceptable carrier therefor.

* * * * *